United States Patent [19]

Palm et al.

[11] Patent Number: 5,276,546
[45] Date of Patent: Jan. 4, 1994

[54] THREE DIMENSIONAL SCANNING SYSTEM

[75] Inventors: Steven G. Palm, Minneapolis; Elwin M. Beaty, Minnetonka, both of Minn.

[73] Assignees: Butch Beaty; Elaine Beaty, both of Minnetonka, Minn.

[21] Appl. No.: 945,526

[22] Filed: Sep. 16, 1992

Related U.S. Application Data

[62] Division of Ser. No. 703,285, May 20, 1991, Pat. No. 5,173,796.

[51] Int. Cl.⁵ .............................................. G02B 26/08
[52] U.S. Cl. ..................................... 359/202; 359/210; 359/900; 358/208; 250/234
[58] Field of Search ...................... 359/201–; 250/234–; 356/379–; 318/632; 358/205, 206, 208, 474

[56] References Cited

U.S. PATENT DOCUMENTS 4,714,830 12/1987 Usui ...................................... 359/202
5,032,924 7/1991 Brown et al. ......................... 358/208

Primary Examiner—Martin Lerner
Assistant Examiner—James Phan
Attorney, Agent, or Firm—Leone & Moffa

[57] ABSTRACT

A part scanning and part calibration method for the inspection of printed circuit boards and integrated circuits includes a camera and two rotating mirrors to scan an image of a pattern mask retical upon which a precise pattern has been deposited. Small parts are placed upon the retical to be inspected. The third overhead mirror is provided to view the part under inspection from another perspective. The scene of the part is triangulated and the dimensions of the system can thus be calibrated. A precise retical mask is provided with dot patterns which provide an additional set of information needed for calibration. By scanning more than one dot pattern the missing state values can be resolved using an iterative trigonomic solution.

9 Claims, 11 Drawing Sheets

PATTERN OF CENTER DOT

THREE DIMENSIONAL SCANNING SYSTEM

This application is a divisional of co-pending U.S. application Ser. No. 07/703,285 filed May 20, 1991 entitled 3-D Scanner System, now U.S. Pat. No. 5,173,796.

This invention relates to a three dimensional ("3-D") scanner and, more particularly, to a line scanning calibration apparatus involving a single camera with two rotatable mirrors and a third overhead mirror.

BACKGROUND OF THE INVENTION

Prior art 3-D line scanners have involved multiple access mirrors and multiple cameras. Scanners have been used to inspect printed circuited boards integrated circuits and other small parts. The prior art requires two cameras and a multiple number of mirrors to accomplish the scanning mechanism. Traditional prior art scanning algorithms utilize a triangulation method that requires two mirrors. Multiple cameras increase the cost of prior art solutions as well as the complexity.

Prior art part scanning apparatus, have utilized a "golden part" for calibration of the scanning operation. A golden part is a part that is precisely dimensioned in a coordinate system, as for example, a Cartesian coordinate system using x, y, and z coordinates. The golden part provides an extremely precise image of the parts that are to be inspected with the scanner. The golden part typically is extremely expensive to produce and in some cases very difficult to produce. A unique golden part must be produced for each unique part design. The difficulty and expense arises from the need to provide a golden part that has extremely high tolerances, sometimes less than 10 millionths of an inch. Such precision is required for each different golden part created.

The golden part is scanned by the scanner of the prior art and is used to create a "trained image". The trained image is then used to match up a image of an inspected part to calibrate the scanner of the prior art. The prior art method requires a golden part to have at least 10 times more accuracy than the part to be inspected. It is therefore one motive of the invention to eliminate the need for the construction of a "golden" part for each and every part to be inspected by the part scanning apparatus.

SUMMARY OF THE INVENTION

The invention provides a method of inspecting a three dimensional part using a single axial camera that receives an optical input through a set of two mirrors. A third mirror is provided to provide a top view of the part. The mirrors are precisely rotatable such that the operator is aware of the exact location of the mirror. The mirrors are calibrated with a method of the invention using a novel triangulation technique. The calibration method proceeds by first noting the position of the two rotatable mirrors and the position of the camera. A precise auto-focus mechanism is incorporated that allows the feedback of focus vs. distance information to the controller of the system. During calibration a precisely defined object such as a reticle mask is employed to provide a set of dimensional data that is invariate over the system parameters. The reticle mask has a precise pattern whose featured dimensions are precisely known. The calibration method proceeds by creating a set of state equations that completely describe the ray of light traversing from the camera through the first and second mirrors and onto the reticle. The ray of light is assumed to be focused from the auto-focusing mechanism at a predetermined relative distance. The calibration method of the invention proceeds by then introducing a third overhead mirror that provides a second set of state equations. The first and second set of state equations can then be solved using an iterative method whereby unknown values of the states can be determined by algebraic manipulation.

It is one object of the invention to provide an improved method of part inspection that utilizes a single camera to analyze the part in three dimensions.

It is yet another object of the invention to provide an improved line scanner that can inspect parts in three dimensions using a precisely defined reticle mask.

It is yet a further object of the invention to provide an improved part scanning mechanism that is lower in cost.

It is yet a further object of the invention to provide an improved scanning mechanism that allows the three dimensional characterization of a part.

It is yet a further object of the invention to provide an improved part scanning calibration system that can be auto-focused and does not need manual intervention.

It is yet a further object of the invention to provide an improved part scanning mechanism which provides for a single camera with two precisely located mirrors and which correlates the rotational angle of each mirror to the displacement in a focused image of a mask reticle.

It is yet a further object of the invention to provide an improved line scanning mechanism whereby the second triangulation camera is eliminated.

It is yet another object of the invention to provide a part scanning calibration mechanism that does not require use of a golden part.

It is yet another object of the invention to provide a reticle mask that has small pattern features that have been photo-deposited on a plate with high accuracy.

It is yet a further object of the invention to use a lower cost lower resolution camera as the optical detector of the system.

It is still a further object of the invention to provide an improved dot scanning system whereby the edge of a dot is found using an edge detection algorithm.

It is yet a further object of the invention to use an auto-focusing camera to determine the path length of a ray of light reversing from an object to be scanned in the camera.

DETAILED DESCRIPTION OF THE PREFERRED EMBODIMENT

Figure 1:
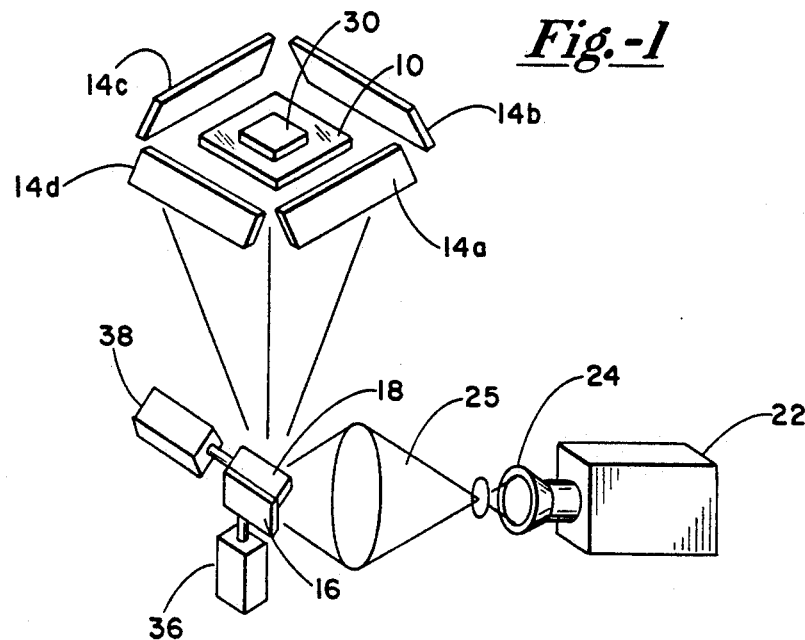
FIG. 1 is a schematic diagram of the apparatus of the invention.

FIG. 1 shows the method and apparatus of the three dimensional scanning system of the invention. FIG. 1 shows a CCD camera 22 with an auto-focusing zoom lens 24. The auto-focusing zoom lens 24 is trained on an optical system 25 that views a set of mirrors. The set of mirrors are composed of a Y axis mirror 16 and an X axis mirror 18 gazing on a set of 4 overhead mirrors 14A, 14B, 14C and 14D as well as a reticle 10 having a generally planar shape. The Y mirror 16 is controlled by a Y servo-motor 36. The X mirror 18 is controlled by an X servo-motor 38. The reticle 10 is used as an optically transmissive support for a part 30 to be scanned. The mirror's optical system 25 and auto-focusing zoom lens 24 provide an image of the part as well as an image of the reticle 10. The mirror system described above provides an apparatus that can view the part from above and below a plane defined by the reticle 10.

Figure 2:
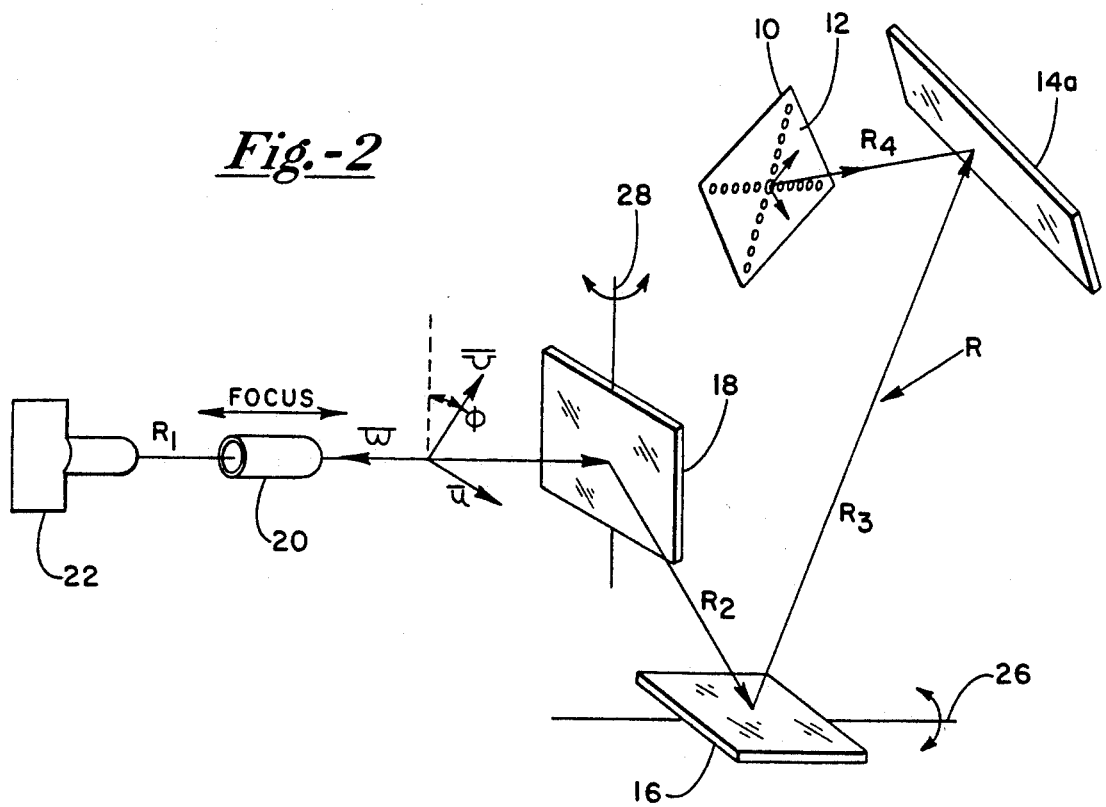
FIG. 2 is a three dimensional perspective representation of the retracing method of the invention.

FIG. 2 shows a three dimensional perspective schematic representation of one embodiment of the apparatus of the invention used to scan and calibrate an optical scanning system. The apparatus of the invention includes a camera 22 which receives an image through an auto-focusing zoom lens 20. The auto-focusing zoom lens 20 provides a means to focus a set of incoming optical rays R into the lens of camera 22. The auto-focusing mechanism provides a relative means of determining the path length of an optical ray in that there is a relationship between the distance where an object will become focused and the amount of focusing adjustment done by the optical automatic auto-focusing system. In the method of the invention the reticle 10 has deposited upon it a pattern 12. The pattern 12 provides a number of features for the invention. The reticle pattern 12 provides a means to accurately access the size and relative position of images in the optical system. The analysis of the method of the invention proceeds by analyzing the tracing of an optical ray from the target to the imaging device. In the diagram of FIG. 2 the ray is proceeding from the reticle pattern to the overhead mirror 14A to the Y mirror 16 then to the X mirror 18, then through the auto-focusing system, then to the camera. Each ray R4, R3, R2 and R1 has associated with it three dimensional coordinates XYZ.

When the apparatus of the invention is first turned on it requires calibration. In the method of calibration provided by the instant invention, the positions of the X and Y mirrors are known precisely as well as the position of the camera 22. The calibration mechanism takes advantage of the fact that the pattern on the reticle provides a precise image in the CCD camera 22. The angular displacements of the X and Y mirror shown around the Y mirror axis 26 and the X mirror axis 28 are not known before calibration. Also, the location of the overhead mirror 14A and its angular inclination with respect to the optical ray R3 is not known. The method of the invention proceeds by characterizing the optical ray R traversing through the mirrors and optical systems and creating a set of system equations that can be solved for unknown variables. The precisely created reticle 12 provides the information needed to solve the system of equations for the precise location of the overhead mirror 14A and the optical axis 26 of the Y mirror and the optical axis 28 of the X mirror. In the calibration of the invention the reticle is viewed in two different sets, first it is viewed from the bottom using the rotatable mirrors. And secondly, it is viewed from the top using the overhead mirror. The two views are necessary to scan the parts 30 in 3 dimensions. The bottom view provides a precise profile view of the object. The bottom view or the plane of the reticle 10 is defined in the optical system as the $Z=0$ position.

Figure 3:
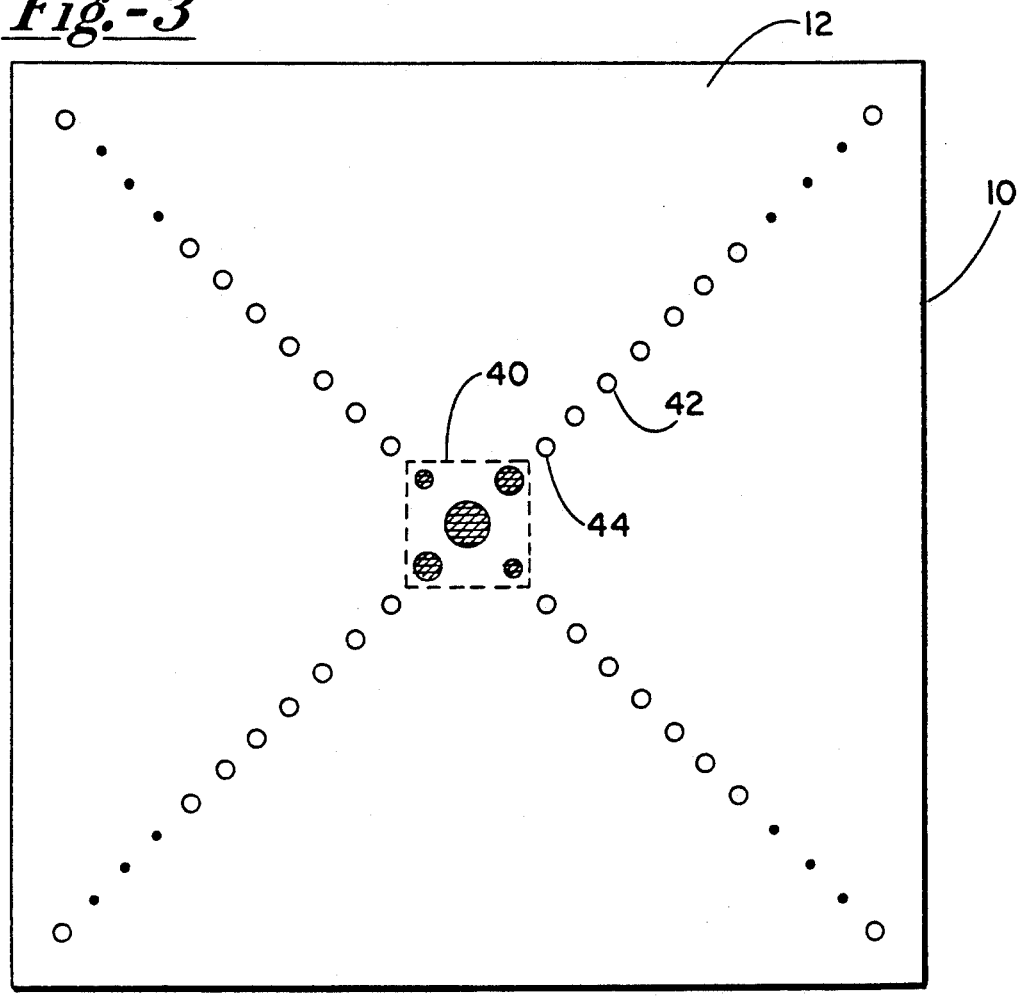
FIG. 3 is a representation of the mask reticle pattern as employed in one embodiment of the invention.

Now referring to FIG. 3, the precise reticle pattern 12 is shown. The precise reticle pattern 12 is drawn or advantageously photo-deposited on reticle 10. The pattern shows a precise geometry that can be used to accurately calibrate the optical system of the method of the invention. The reticle pattern is a diagonal set of circles or dots, for example, that are precisely spaced and have a precise size. All features on the reticle have a known shape and a known size. The size and shapes and locations are predetermined prior to the calibration of the invention. Other sizes and shapes may be employed to accomplish the function of the reticle 10 and the description herein is meant by way of example and not limitation. The center of the pattern comprises a pattern of 5 dots 4 within the broken line used for the initial calibration of the apparatus of the invention. A second dot 44 is used to determine the orientation of the reticle space relative to the center dot pattern 40. Other dots shown here as 42 are used to characterize the reticle plane. The position of the dots are defined as $Z=0$ everywhere on the reticle 10, that is, the reticle is assumed to be a plane in three dimensional space and the plane that the reticle exists in is defined as the $Z=0$ plane.

Figure 4:
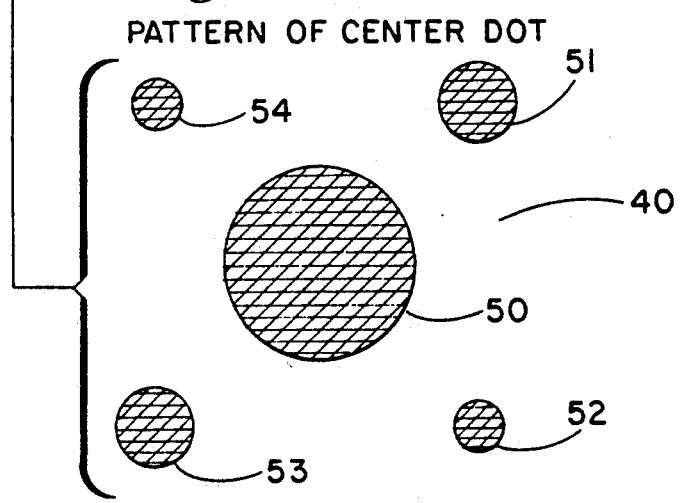
FIG. 4 is a representation of the dot pattern of the center dot of the precision reticle mask as employed in one embodiment of the invention.

Now referring to FIG. 4 which shows a detail enlargement of the center dot pattern 40 of FIG. 3. The center grouping of dots 40 shows a large central dot 50 surrounded by four peripheral dots 51, 52, 53 and 54. The large center dot 50 is used by the focusing and positioning system of the invention to accurately locate and position the center of the reticle. This dot is predetermined to be at the center of the reticle 10. The peripheral dots 52 and 54 are used as diagonal positioning dots as well as the dots 53 and 51. The size of the dots are varied to indicate rotational position of the reticle in that dot 53 is different in size from dot 52. Dot 54, 52 and 51 are different sizes but are advantageously smaller than dot 53. Those skilled in the art will understand that this mask pattern is provided as one method of fixing a three dimensional precise shape in that other patterns can be used to provide a precise shape such as cross hatching or linear lines with cross tick marks.

Figure 5A:
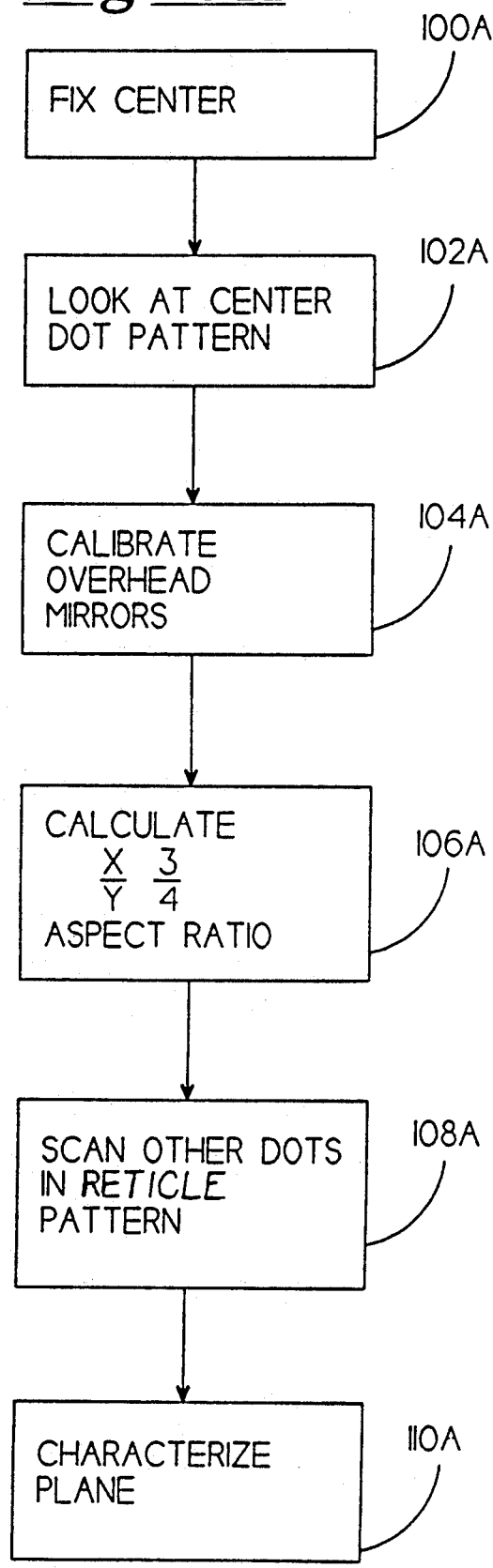
FIG. 5A and 5B illustrate methods of calibrating the invention shown in a high level flow diagram.
Figure 5B:
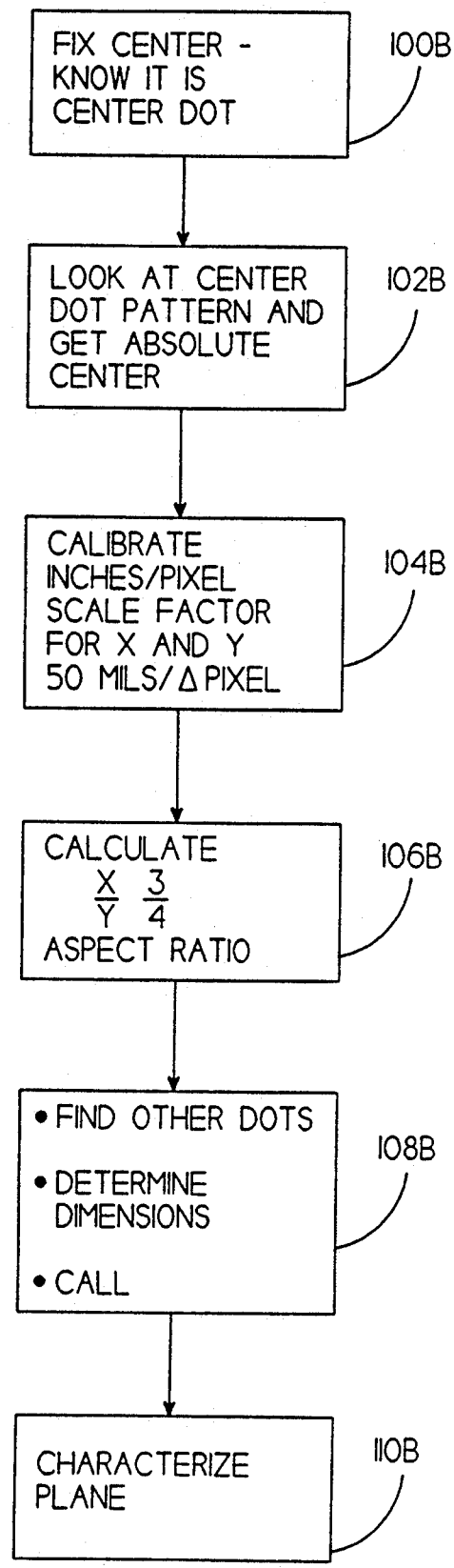

Referring now to FIG. 5B, a high level flow diagram of the calibration method of the invention is shown. The process of calibrating the invention first starts at block 100B by fixing the center of the center dot pattern 40 shown. The process then flows to block 102B wherein the optical system looks at the center dot pattern and obtains an absolute center from the pattern 40. The process then flows to block 104B where the display and camera are calibrated to calculate a scale factor for the X and Y directions. The process then flows through schematic block 106B where the aspect ratio of the camera is determined as the dimension X divided by the dimension Y. The process then flows to 108B where the other dots are determined. The other dots are found and their sizes determined which orients the reticle pattern and is used to calculate the characterization of the rest of the optical system. The process then flows to block 110B wherein the rest of the reticle pattern is characterized and the optical system is calibrated. Each block will in turn be detailed with reference to the following FIGS. 6, 7, 8 and 9.

Now referring to FIG. 5A showing the method of calibrating the invention's top mirror shown in FIG. 1 as mirrors 14A, 14B, 4C and 14D. The method of the calibrating the top mirrors is similar to the method of calibrating the reticle pattern and the method of calibrating the axis of the X mirror 28 and Y mirror 16 as shown in FIG. 2. Similar to the reticle and axis alignment process shown in FIG. 5B, the process in FIG. 5A starts, at block 100A, by fixing the center of an image on the CCD and processing the rays from the image into the CCD camera. The method of looking at the center dot is described in FIG. 7. The advantage at this point in the calibration method of the invention is that the axial mirror displacements have now been calibrated, the axial mirror axis' shown on FIG. 2 as 28 for the X mirror and 26 for the Y mirror. This enables the apparatus and method of the invention to calibrate a third unknown optical surface which is the overhead mirror 14A shown in FIG. 2. The process of FIG. 5A then flows to looking at the center of the dot pattern, in step 102A. The optical axis and the focal optical path lengths from the image can be correlated using the methods of FIG. 16. At to step 102A, the dot pattern absolute center is determined by edge detection. Those skilled in the art will recognize that certain methods of edge detection such as subpixel edge detection could be used to more accurately find the position of the dots. Those skilled in the art will understand that alternative methods of edge detection could also be used. The process then flows to box 104A where the position of the overhead mirrors are determined by using the optical path of the mirror and solving for the state variables of the ray tracing equation. Ray tracing and vector analysis is well known in the art. A good description of vector analysis can be found in a book entitled *Introduction to Vector Analysis* by Harvey F. Davis and Arthur David Snyder, 4th Edition, published by Allyn and Bacon, Inc. A good review of retracing can be found in a December 1990 Byte article entitled *Retracing for Realism*, in which the mechanism of retracing is described. Both articles are hereby incorporated by reference. The process then flows to 106A where the aspect ratio's are calculated again. The process then flows to 108A in which the other dots in the reticle pattern are scanned and the overhead mirrors are further characterized. The process then flows to 110A where the plane of the reticle is characterized.

Figure 6:
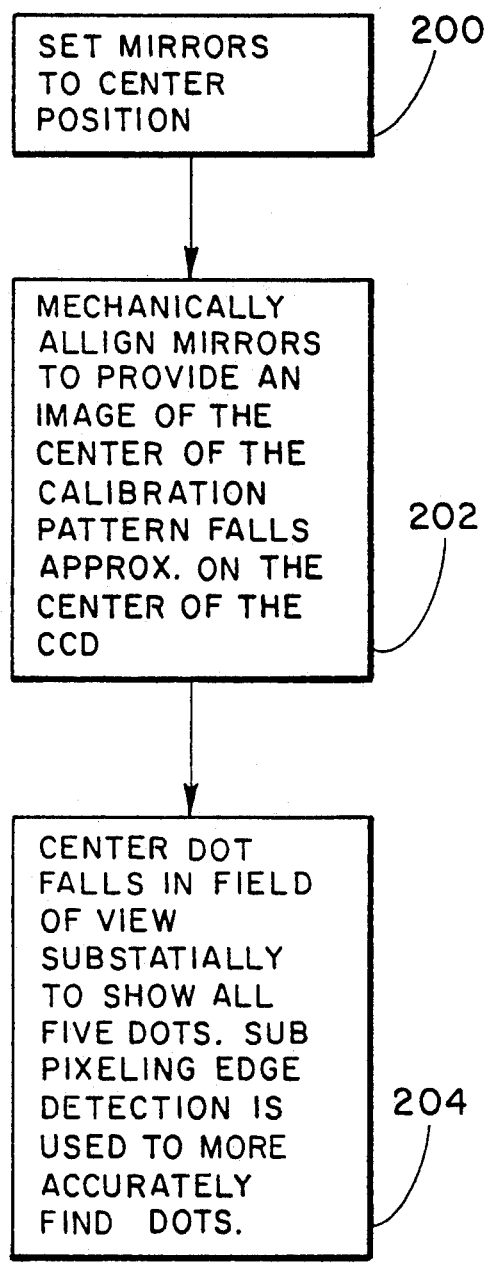
FIG. 6 is a flow diagram showing a method of fixing the center of a dot as employed by the invention.

FIG. 6 shows a flow diagram for fixing the center dot pattern 40 which is shown as block 100A and 100B in FIG. 5A and 5B, respectively. The system first sets the mirrors 16, 18 to their center positions in block 200. All apparatus references refer to FIGS. 1 and 2. The X mirror 18 and the Y mirror 16 are positioned such that if they rotated either way an equal amount, their deflections would be roughly in the center. The process of fixing the center then flows to block 202 where the mirrors 16, 18 are mechanically aligned to provide an image of the center of the calibration pattern so that it falls directly on the center of the CCD array in CCD camera 22. The alignment of the mirrors allows the mechanisms that move the mirrors 16, 18 to adequately provide a range of motion that scans both the CCD camera 22 and the object or part 30 on the reticle. The process of fixing the mirrors then flows to 204 where the center dot falls on the field of view of the CCD camera to substantially show all five dots in the center dot pattern 40. The process then flows to 102A, 102B in FIGS. 5A and 5B to look at the center dot pattern.

Figure 7:
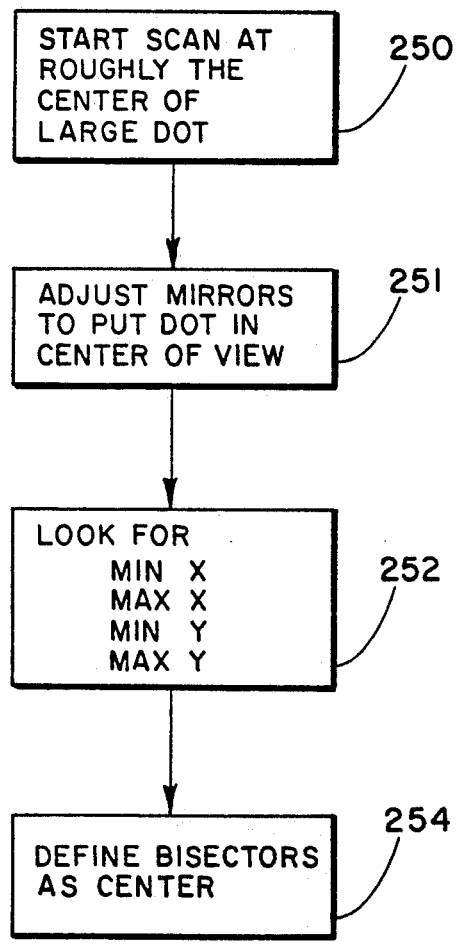
FIG. 7 is a schematic flow diagram of the method of looking at a center of a dot as employed in one embodiment of the invention.

Referring now to FIG. 7, the method of determining the position of the center dot 50 is shown. The process starts at block 250 where the scan of the pattern is roughly at the center of the large dot. The process then uses conventional edge detection techniques that look for a minimum X and a minimum Y and maximum X and maximum Y for the dot. The mirrors are adjusted in process block 251 to locate the dot in the center view of the CCD camera 22. After the minimum X, minimum Y and maximum X and maximum Y are determined from edge detection methods known in the prior art, (block 252) the bisectors of the centers are found and the precise center of the dot is determined in process block 254.

Referring back to FIGS. 5A and 5B, the scale factors of the invention of the apparatus are determined by dividing the number of mils by the number of pixels. This is determined by knowing that the center dot pattern 40 is a certain size, for example, in this case 50 mils and the number of pixels that cross the center are known. In this case, for example, 100 pixels indicates that the mils per pixel to be 50/100 or the aspect ratio would be ½. The same procedure can be used to determine the scale factor for Y. The process then flows to block 106A, 106B to calculate the aspect ratio of Y to X. The process then flows to 108A, 108B where the other dots are scanned and the dimension of the precise reticle pattern are used to calibrate the optical system.

Figure 8:
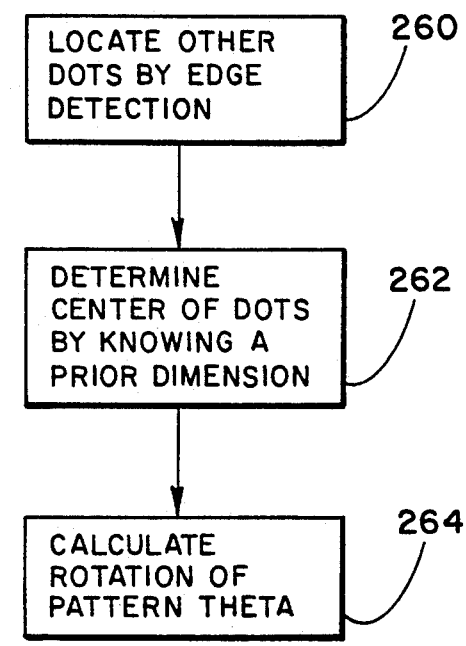
FIG. 8 is a schematic flow diagram of the method of calculating the angle of a mirror.

FIG. 8 shows the method of calculating the angular displacement of the mirrors knowing the size and relative aspect ratios of the pixels in the invention. In block 260 another dot is found by edge detection. The edge detection method of the invention is outlined in FIG. 7. The additional dot's position is in a predetermined known location. This provides a method of determining a system of equations for the first dot and the second dot (block 262). The absolute position of the two dots are known which provides sufficient information to determine the angular displacement verses linear displacement of the object on the CCD screen (block 264).

Referring now to FIG. 2 which shows the Y mirror 16 and the X mirror 18 undergoing a reflection of a ray R, compared to R1, R2, R3 for every displacement of mirror X and mirror Y the image associated will move in a certain direction. By watching the motion of the relative dot on the screen, the location and calibration of mirrors can be accomplished. For every angular displacement of the Y mirror there will be an associated Y linear displacement of the image. For every angular displacement of the X mirror there will be an associated displacement of the X image.

Figure 9:
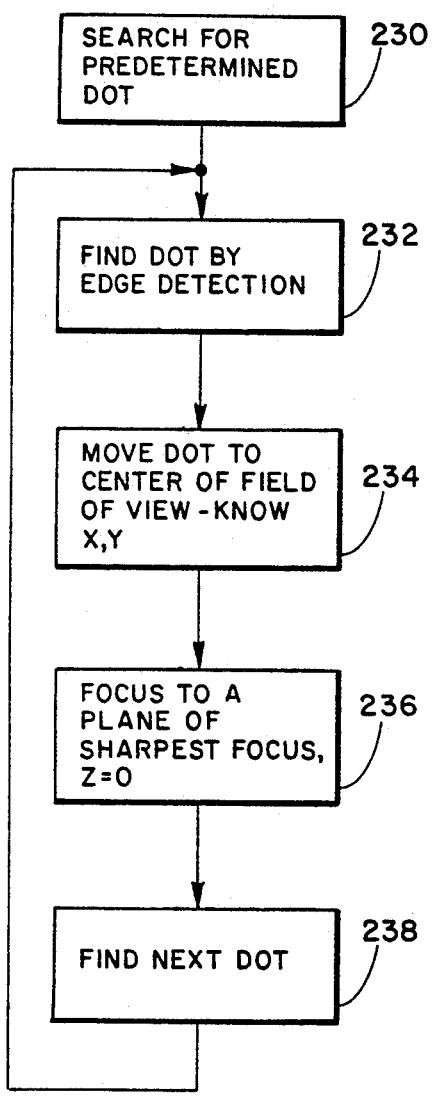
FIG. 9 is a schematic flow diagram method of one example of the characterizing the plane for all dots on the reticle.

Referring now to FIG. 9 where the characterization of the Z=0 plane is accomplished. In step 230 the remainder of the dots are checked and searched for. Each dot is found by edge detection as shown in FIG. 6 process step 232. The process then moves to step 234 where each dot is positioned to the center of the field of view and the location of the dot is memorized. The process then flows to step 236 where the plane of sharp is focused Z=0 is determined. The length of the optical path can now be related to the distance that the Z plane is determined to be by defining the Z plane to be 0 at this location. The process then flows to block 238 where the next dot is found and the same process is repeated back to step 232.

Figure 10:
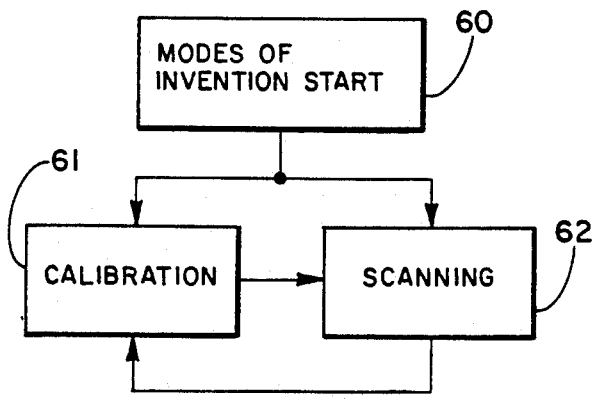
FIG. 10 is a mode diagram of the operation of the invention.

Referring now to FIG. 10, two modes of the operation of the invention are shown. The invention is shown starting in the start mode 60 and either can go immediately into the scanning mode 62 or the calibration mode 61. If the invention is in calibration mode 61 it can at any time go into the scanning mode 62. The invention, while in scanning mode can any time go into the calibration mode 61. Thus, the invention provides a method of automatically calibrating and scanning dynamically during the operation of a scanning operation. The invention thus provides a way of compensating for temperature variations in the optical characteristics of the materials as well as in a vibrational related changes or simply changes due to moving the part or moving the apparatus.

Now referring to Table A which shows a listing of the model for the method of the invention. The invention utilizes a model structure of the apparatus of the invention that forms a computing structure. The models are given below as a list of data types with data representations and line numbers. The first model is the model of the optical system of the method of the invention. The elements of the model consist of a type which tells what kind of model type it is. In line 422 a unit-type which tells what kind of unit-type it is. In line 423 a model label which labels the model in 424 is given. In line 425 a calibration time for the model which is given. In line 426 a number of surfaces in the model which is given. The surface structure is described below in line 427. The number of different paths that there exist in the model are described in line 428. The optical path structure is given in line 430. The next line is a two dimensional array that defines a viewpoint at the optical origin. The next model element is the camera roll angle at line 434 which describes the angle between the original view and the X axis in world coordinates. The next element of the model is on line 437 which is the focusing model which is described below. The final element of the model is the mirror model which is a mirror model structure described below.

TABLE A

| | | |
|---|---|---|
| 419 | /* Model structure */ | |
| 420 | struct MODEL | |
| 421 | { | |
| 422 | BYTE Type; | /* model type */ |
| 423 | BYTE UnitType; | /* unit type */ |
| 424 | char Label[LABELSIZE]; | /* model label */ |
| 425 | time_t CalibTime; | /* last time & date the system was calibrated */ |
| 426 | BYTE NumberOfSurfaces; | /* number of different surfaces in model */ |
| 427 | struct SURFACE[MAXSURFACES]; | /* array of surfaces */ |
| 428 | BYTE NumberOfPathes; | /* number of different pathes in model */ |
| 429 | /* array of optical pathes */ | |

TABLE A-continued

| | | |
|---|---|---|
| 430 | struct OpticalPath[MAXOPTICALPATHES]; | |
| 431 | /* the unit vectors u,v,w that define the view plane at the optical origin */ | |
| 432 | double OriginViewUnit[VECT3] [VECT3]; | |
| 433 | /* angle between OriginViewVector u and x axis world vector(1,0,0) */ | |
| 434 | float CameraRollAngle; | |
| 435 | /* the ratio of ViewDim[U]/ViewDim[V]; assumed constant for all views */ | |
| 436 | double AspectRatio; | |
| 437 | struct FOCUSMODEL FocusModel; | |
| | /* structure describing focus */ | |
| 438 | struct MIRRORMODEL MirrorModel[VECT2]; | |
| | /* x & y moving mirror models */ | |
| 439 | }; /* end od struct MODEL */ | |

Now Table B refers to a structure for the surface of a optical element in the system. Table B lists a surface type whether it is reflective or refractive in line 388. The surface has a label on line 389, the refractive index of the surface is given on 390, the position in the world of the surface is given in line 391. The normal vector is given on line 393 which is the unit world vector normal to the surface anchored at the position vector given on line 391.

TABLE B

| | | |
|---|---|---|
| 385 | /* Optical Surface structure */ | |
| 386 | struct SURFACE | |
| 387 | { | |
| 388 | BYTE Type; | /* surface type: REFLECT, REFRACT */ |
| 389 | char Label[LABELSIZE]; | /* surface label */ |
| 390 | float RefractiveIndex; | /* refractive index, past the surface */ |
| 391 | double Position[VECT3]; | /* world surface position */ |
| 392 | /* unit world vector normal to the surface anchored at the position vector */ | |
| 393 | double Normal[VECT3]; | |
| 394 | }; /* end of struct SURFACE */ | |

Table C refers to the optical path structure which details an optical path in an ordered list of surfaces.. The optical path contains a type on line 407, a label on line 408, a lightswitch byte on line 409 and another surface byte on line 410, a surface index structure byte on line 411, and a surface structure on line 413 which has been previously described.

TABLE C

| | | |
|---|---|---|
| 402 | /* Optical Path Structure */ | |
| 403 | /* an optical path is a ordered list of surfaces */ | |
| 404 | /* optical path types are the same as scan types */ | |
| 405 | struct OPTICALPATH | |
| 406 | { | |
| 407 | BYTE Type; | /* optical path type */ |
| 408 | char Label[LABELSIZE]; | /* optical path label */ |
| 409 | BYTE LightSwitches; | /* bite to turn for lights */ |
| 410 | BYTE NumberOfSurfaces; | /* number of surfaces along the path */ |
| 411 | BYTE SurfaceIndex[MAXSURFACES]; | /* array of indexes to the surfaces */ |
| 412 | /* array of pointers to the surfaces in the optical path */ | |
| 413 | struct SURFACE far *SurfacePtr[MAXSURFACES]; | /* not dynamically allocated */ |
| 414 | }; /* end of struct OPTICALPATH */ | |

Now referring to Table D which is a focusing model structure. The focus model contains three elements which determine the focus of the ray traced in the method of the invention. The first element is a coefficient V which is a one dimensional vector of polynomial coefficients used to compute V of the view dimension vector from the focus position using the routine that will be described below. The next element is a coefficient of W which is a one dimensional vector which is a vector of polynomial coefficients used to compute W of the view dimension vector from the focus position and the final element is defined on line 358 as a coefficient of the optical path length which is a one dimensional vector of polynomial coefficients used to compute the optical path length from the focus position.

TABLE D

| 347 | /* Focus Model Structure */ | |
|---|---|---|
| 348 | struct FOCUSMODEL | |
| 349 | { | |
| 350 | /* polynomial coefficients used to compute V of the ViewDim vector */ | |
| 351 | /* from the focus position | */ |
| 352 | float CoeffV[VECT3]; | */ |
| 353 | /* polynomial coefficients used to compute W of the ViewDim vector */ | |
| 354 | /* from the focus position | */ |
| 355 | float CoeffW[VECT3]; | |
| 356 | /* polynomial coefficients used to compute the optical path length(opl) */ | |
| 357 | /* from the focus position | */ |
| 358 | float CoeffOPL[VECT3]; | |
| 359 | }; /* end of struct FOCUSMODEL */ | |

Table E describes a mirror model structure which is simply a one dimensional vector of coefficients that contain the polynomial coefficients to compute the mirror angles from a mirror position.

The foregoing tables describe the optical system of the method of the invention with regard to the elements of the structure of the invention disclosed above and in relation to the full programming model of the invention listed in Appendix A. Line numbers in Tables A, B, C, D and E correspond to line numbers in the C programming language code found in Appendix A.

TABLE E

| 361 | /* X & Y Mirror Model structure */ |
|---|---|
| 362 | struct MIRRORMODEL |
| 363 | { |
| 364 | /* polynomial coefficients to compute mirror angles from mirror position */ |
| 365 | float Coeff[VECT3]; |
| 366 | }; */ end of struct MIRRORMODEL */ |

Figure 11:
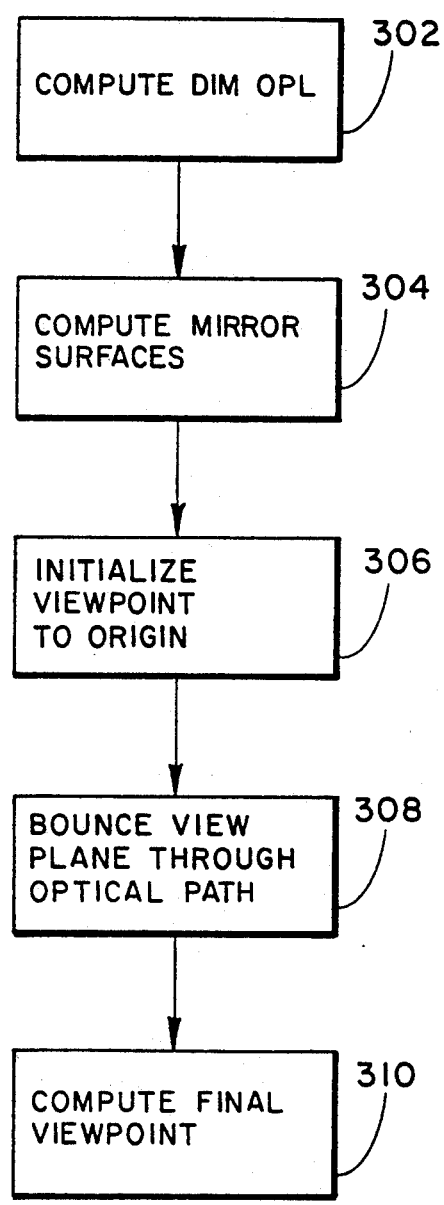
FIG. 11 is a process flow diagram for computing the view plane.

Referring now to FIG. 11, a flow diagram of a method of computing the view plane as contemplated by the present invention is shown. The method comprises the steps of computing dimensions and optical path length ("OPL") 302, computing the location of the X,Y mirror surfaces 304, initializing a view point to origin 306, bouncing the view plane through the optical path 308 and computing the final view point 310. At step 302 the algorithm computes the dimensions and optical path length. Once the optical path length is known the process proceeds to step 304 where the location of the mirror surfaces for mirrors 16 and 18 are determined. Having determined the mirror surface locations, the method proceeds to step 306 wherein the view point is initialized to be the origin at coordinates 0,0,0. Next, at step 308 the view plane is reflected or bounced through the optical path. The final view point can then be computed at step 310.

Figure 12:
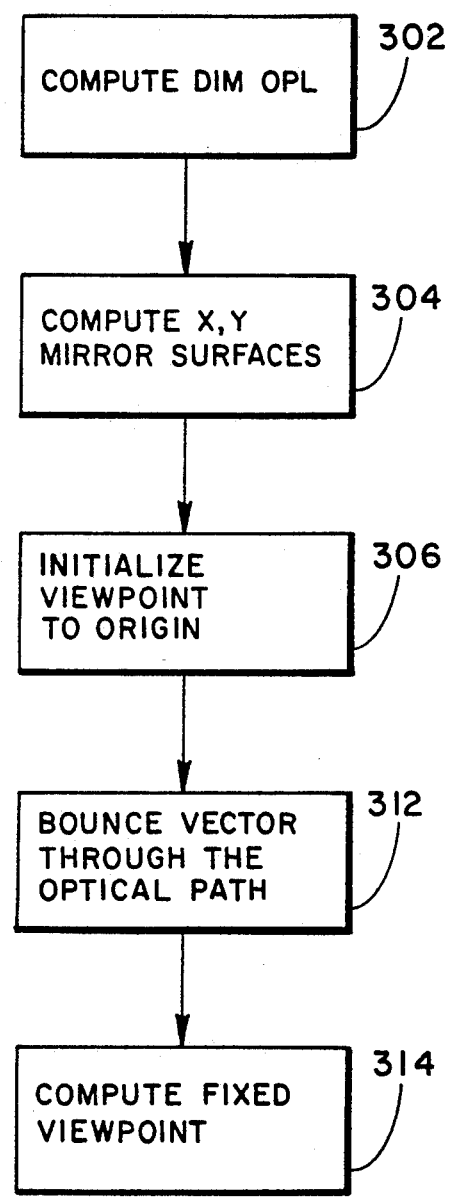
FIG. 12 is a process flow diagram for computing the view point.

Referring now to FIG. 12, a flow diagram of a method of computing the view point as contemplated by the present invention is shown. The method comprises the steps of computing dimensions and optical path length ("OPL") 302, computing the location of the X,Y mirror surfaces 304, initializing view point to origin 306, bouncing a vector through the optical path 312 and computing the final view point 314. At step 302 the algorithm computes the dimensions and optical path length. Once the optical path length is known the process proceeds to step 304 where the location of the mirror surfaces for mirrors 16, 18 are determined. Having determined the mirror surface locations, the method proceeds to step 306 wherein the view point is initialized to be the origin at coordinates 0,0,0. Next, at step 312 a vector is reflected or bounced through the optical path. The final view point can then be computed at step 314.

Figure 13:
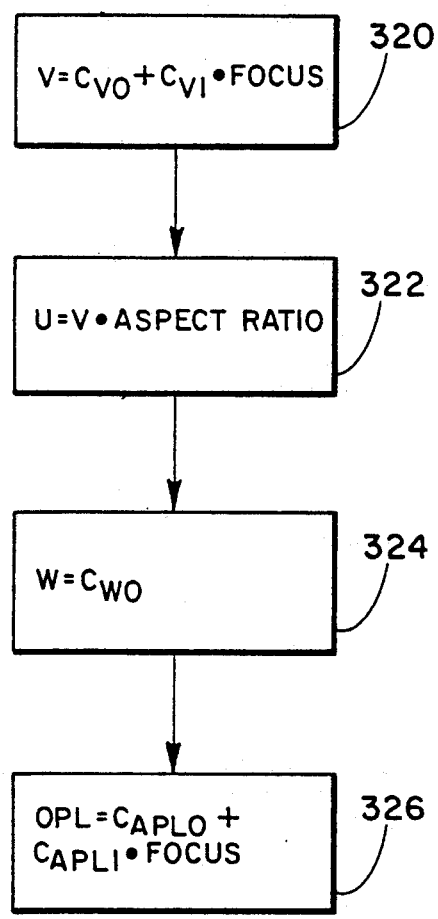
FIG. 13 is a process flow diagram for computing the OPL coefficient.

Referring now to FIG. 13, a flow diagram of a method of computing the dimensions and optical path length as contemplated by the present invention is shown. The method comprises the steps of computing the parameters V at step 320, U at step 322, W at step 324 and OPL at step 326. Starting at step 320 V is found by computing the equation $$V = C_{v0} + C_{v1} * \text{focus}.$$

Then, at step 322 U can be solved according to the equation $$U = V * \text{Aspect ratio}.$$

Next, at step 324 W is solved by the equation $$W = C_{w0}.$$

Finally, the optical path length OPL can be determined by $$OPL = C_{opL0} + C_{opL1} * \text{focus}.$$

The above symbols are described below:
$C_{v0}$: Coefficient of View Plane Equation - Units of Inches
$C_{v1}$: Coefficient of View Plane Equation Focus Unit -Units of Inches - Dimension change depending on focus position
focus: Position of the Focus Element
V: Length of the distance from the view point to the view plane.
Aspect ratio: Radio of U/V
W: Out of the view plane in right hand coordinate system. W is the perspective point. $C_{w0}$ is length of W.
OPL: Optical path length - Total distance of the optical path length in inches
$C_{opL0}$: Coefficient determined in calibration system
$C_{opL1}$: Coefficient determined in calibration system.

Figure 14:
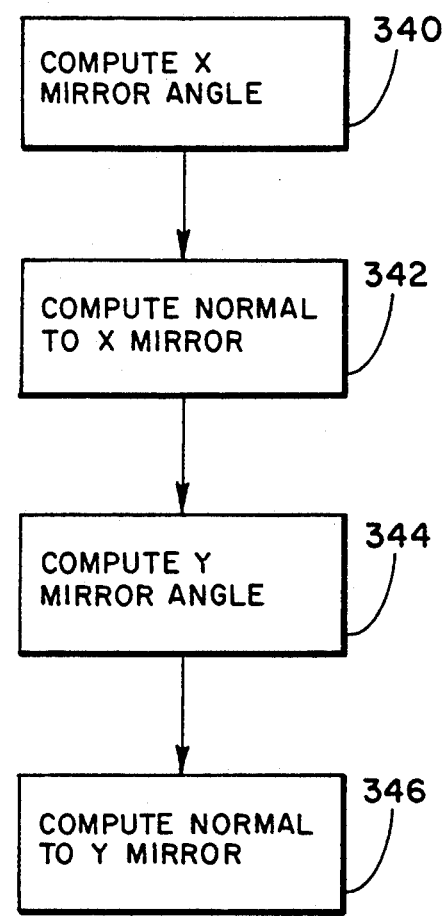
FIG. 14 is a process flow diagram for computing the mirror surfaces.

Referring now to FIG. 14, a flow diagram of a method of computing the location of the mirror surfaces as contemplated by the present invention is shown. The steps for this computation include computing the X mirror angle 340, computing the normal to the X mirror 342, computing the Y mirror angle 344 and computing the normal to the Y mirror surface 346.

Figure 15:
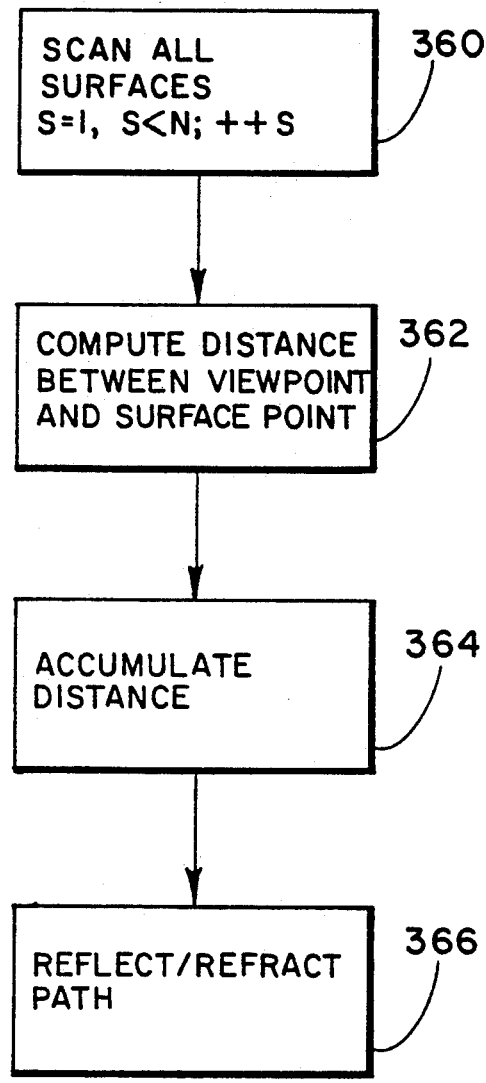
FIG. 15 is a process flow diagram for bouncing the view plane through the optical path.

Referring now to FIG. 15, a flow diagram of a method of bouncing the view plane through the optical path as contemplated by the present invention is shown. The steps comprise scanning all surfaces 360, computing the distance between the view point and surface point 362, accumulating the distance 364 and reflecting and refracting the path 366.

Figure 16:
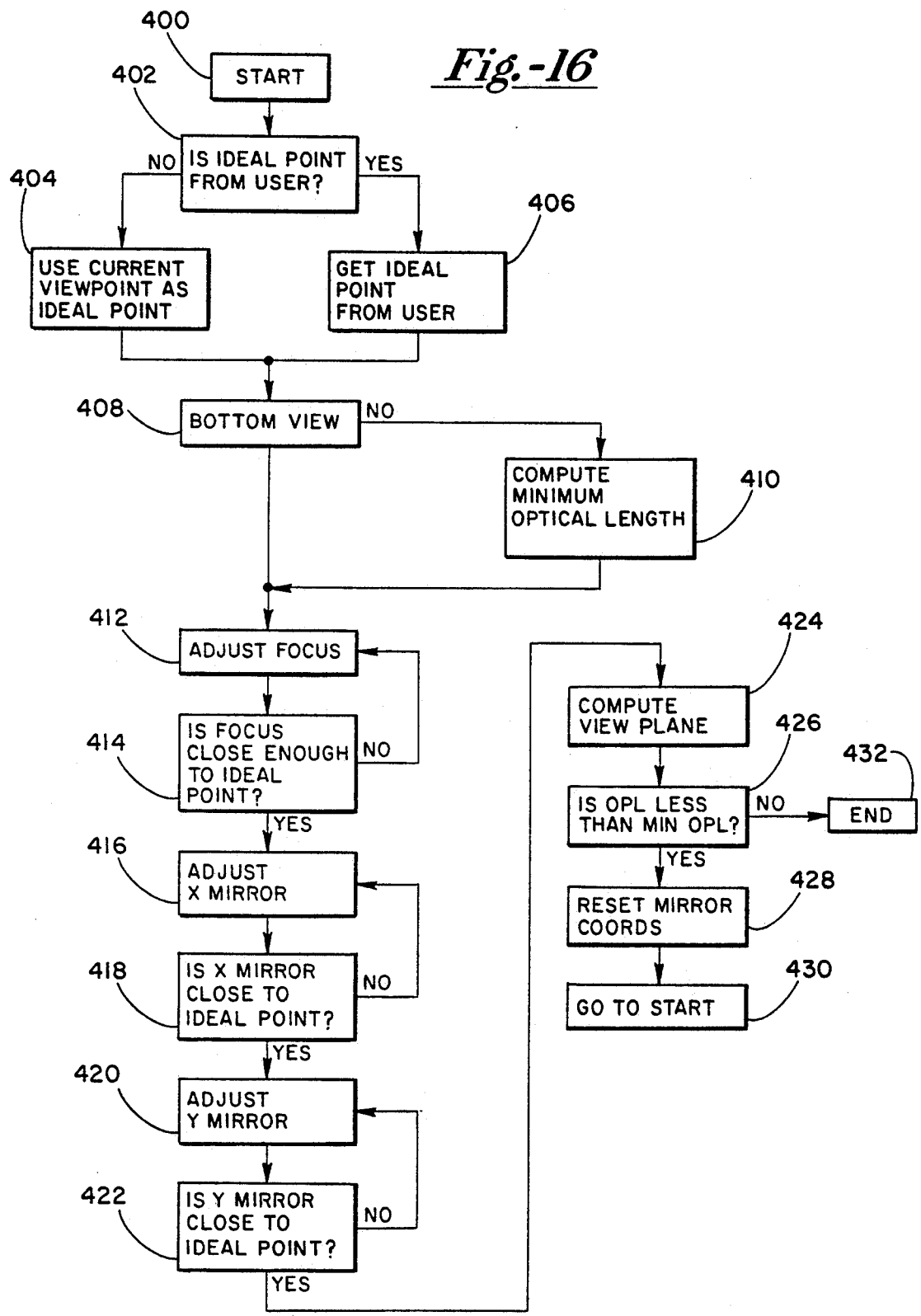
FIG. 16 is a process flow diagram for computing the mirror position.

Now referring to FIG. 16 which shows the method of computing the mirror position from the view point. The method starts at process flow block 400. Process flow block 402 requests whether the ideal point is entered from the user. If it is, the process flows to process flow block 406 to get the ideal point from the user. If the ideal point is not to be gotten from the user in process block 402 the process flows to process block 404 to use the current view point as the ideal point. The process flows in either case to process block 408 to check whether the view is a bottom view. If it is a bottom view the process flows to process block 412 to adjust the focus. If it is not a bottom view the process flows to process block 410 to compute the minimum optical path length. In either case the process flows to process block 412 to adjust the focus. The process then flows to process block 414 to check whether or not the focus is close enough to the ideal point, if it is not the process flows back to process block 412. In process block 412 the focus is adjusted until such time that the focus is close enough to the ideal point. When the focus is close enough to the ideal point the process flows to process block 412 to adjust the X mirror position. The process then flows to process block 418 to check whether the X mirror position is close to the ideal point. If it is not, the process flows to process block 416 to adjust the X mirror position. If in process step 418 the X mirror is close enough to the ideal point the process flows to process block 420 to adjust the Y mirror position. The process then flows to process block 422 to check whether the Y mirror position is close to the ideal point, if it is not the process flows to process block 420 to adjust the Y mirror position. If the Y mirror position is close to the ideal point the process flows to process block 424 to compute the view plane. The process flows to process block 426 to check whether the optical path length is less than the minimum optical path length. If it is not, the process ends at process step 432. If the optical path length is not less than the minimum optical path length then the process flows to process block 428 to reset the mirror coordinates. The process than flows to process block 430 to return to the start.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A scanning method for scanning an object located in space in up to three dimensions in a scanning system including an image registering means, a first reflecting means, a second reflecting means, and means for calibration including a retical means for registering a pattern having a plurality of positioning indicia thereon wherein each of the plurality of indicia is precisely located with respect to the other indicia on a common plane defined by the pattern of indicia on the calibration means, the scanning method comprising the steps of:
   a. providing a focusing signal, a first servoing signal and a second servoing signal;
   b. automatically focusing onto the object in response to the focusing signal;
   c. operating the first means for reflecting to reflect the object image onto the image registering means wherein the first reflecting means has a first mirror axis and an angular displacement with respect to the first mirror axis and locates the object with respect to a first coordinate axis;
   d. operating the second means for reflecting to reflect the object image onto the registering means wherein the second reflecting means has a second mirror axis and an angular displacement with respect to the second mirror axis and locates the object with respect to a second coordinate axis;
   e. moving the first reflecting means in response to the first servoing signal;
   f. moving the second reflecting means in response to the second servoing signal; and
   g. calibrating the scanning system by focusing on the indicia of the calibration means in a predetermined sequence so as to define a relative position of the common plane with respect to first and second coordinate axes, and wherein a portion of the plurality of indicia form a central calibration pattern of a predetermined size thereon.

2. The scanning method of claim 1 wherein the registering means comprises a CCD camera.

3. The scanning method of claim 1 further comprising the steps of:
   a. locating a plurality of optical reflecting means above the common plane; and
   b. operating the plurality of optical reflecting means so as to provide coordinate information about the calibration means sufficient to locate the common plane in three dimensional space.

4. The scanning method of claim 1 wherein the step of automatically focusing comprises the step of operating a zoom lens to focus onto the object.

5. The method of claim 1 wherein the step of calibrating further comprises the steps of:
   a. aligning and storing the position of the image registering means;
   b. aligning and storing the position of the first reflecting means;
   c. aligning and storing the position of the second reflecting means;
   d. imaging the central calibration pattern so as to view the entire central pattern wherein the pattern image has a first relative image size with an x and y axis;
   e. relating the predetermined size of the central calibration pattern in the x axis to the first relative image size of the image substended by the central calibration pattern on the image registering means to determine an x scale factor;
   f. relating the predetermined size of the central calibration pattern in the y axis to the first relative image size of the image substended by the central calibration pattern on the image registering means to determine a y scale factor;
   g. rotating the first mirror axis and the second mirror axis so as to image any other indicia while storing the amount of angular displacement of the first mirror axis to determine an x axis displacement and storing the amount of angular displacement of the second mirrors axis to determine a y axis displacement;

h. storing an x displacement of the image wherein the x displacement results from the rotation of the first mirror;

i. storing a y displacement of the image wherein the y displacement results from the rotation of the first mirror;

j. relating the x axis displacement to the x displacement to calibrate the first mirror; and k. relating the y axis displacement to the y displacement to calibrate the second mirror.

6. The method of claim 5 wherein all indicia are imaged and calibrated.

7. The method of claim 5 wherein the step of relating the x axis displacement and the x displacement to calibrate the first mirror comprises the fitting of a polynomial.

8. The method of claim 5 wherein the step of relating the y axis displacement and the y displacement to calibrate the second mirror comprises the fitting of a polynomial.

9. The method of claim 5 wherein each indicia is used to calibrate the first and second mirrors.

* * * * *